United States Patent [19]

Winters

[11] Patent Number: 5,004,699

[45] Date of Patent: Apr. 2, 1991

[54] METHOD TO DETECT FUNGI AND YEASTS

[75] Inventor: Mark A. Winters, Mountain View, Calif.

[73] Assignee: SRI International, Menlo Park, Calif.

[21] Appl. No.: 426,538

[22] Filed: Oct. 24, 1989

Related U.S. Application Data

[63] Continuation of Ser. No. 123,389, Nov. 20, 1987, abandoned.

[51] Int. Cl.$^5$ .................. G01N 33/53; C12Q 1/04
[52] U.S. Cl. ................... 435/7.31; 435/34; 435/174; 435/176; 435/805; 435/911; 435/7.5; 435/7.9; 424/3
[58] Field of Search ............... 435/34, 174, 176, 805, 435/911, 7.5, 7.9; 424/3

[56] References Cited

FOREIGN PATENT DOCUMENTS 176355 4/1986 European Pat. Off. .

OTHER PUBLICATIONS

U.S. Army AUA036986, Report 2200, Dec. 1976, pp. 1–13.
U.S. Army ADA020298, Report 2158, Sep. 1985, pp. 1–13.
Galun et al., *Arch. Microbiol.* 108(1):9–16 (1976), p. 1, lines 29–30.
Sharma et al., *Trans. Br. Mycol. Soc.* 69(3):479–83, (1977), p. 2, lines 1–2.
Kaminskyj et al., *Can. J. Bot.* 60(12):2575–80, 1982, p. 2, lines 4–5.
Bracciali, A. et al., in Lectins, Biology, Bichemistry, Clinical Biochemistry, (Bog-Hansen, ed.), Berlin, pp. 633–642 (1982).
Ernst et al., CA87 (10):69568e (1976).
Ernst et al., CA85(14):96713p (1975).
Tokura et al., *Anal. Biochem.* 161, pp. 117–122 (1987).

*Primary Examiner*—Esther L. Kepplinger
*Assistant Examiner*—Toni R. Scheiner
*Attorney, Agent, or Firm*—Irell & Manella

[57] ABSTRACT

A method for detecting organisms such as fungi and yeast in a sample attached to a solid phase, by detecting the presence of chitin in using lectin or anti-chitin antibodies.

19 Claims, 2 Drawing Sheets

METHOD TO DETECT FUNGI AND YEASTS

This application is a continuation of application Ser. No. 07/123,389, filed 20 Nov. 1987, now abandoned.

FIELD OF THE INVENTION

This invention relates to the field of assays to detect target substances, and particularly to assays to determine the presence of pathogenic organisms such as fungi and yeast in a sample.

BACKGROUND

Infections caused by fungi and yeast affect animals including humans, and plants worldwide. One type of fungus, *Trichophyton metangrophytes* causes ringworm. In addition, these organisms contaminate water and food supplies Current methods to detect the presence of contaminating fungi and yeast require obtaining samples from an animal or plant suspected of containing these organisms and culturing the samples to grow any organisms present in the sample in sufficient numbers to readily detect their presence visually. Typically, culturing the organisms requires specialized and costly media and lengthy culture times of up to several weeks. Other methods involve the use of a hot basic solution such as 20% potassium hydroxide to clear smears of specimens on a solid substrate. The cleared specimen is then stained, for example using India ink, then examined by microscope to detect the presence of fungal structures remaining after this treatment.

Fungi and yeasts contain certain substances, including proteins that may be specific for a particular species. Other substances are more widely distributed. For example, chitin (N-acetylglucosamine oligomer) is a polysaccharide component of cell walls found in most fungi and yeasts and is reactive with reagents such as lectins (Galun et al., *Arch. Microbiol.* 108(1):9–16 (1976)).

Assays for the presence of chitin-containing organisms such as fungi are known but have been limited to the detection of chitin using chemical analyses including colorimetric determination (Sharma et al., *Trans. Br. Mycol Soc.* 69(3):479–83 (1977)) and the use of nitrous acid-3-methyl-2-benzothiazolinone hydrazone hydrochloride-ferric chloride and light microscopy (Kaminskyj et al., *Can. J. Bot.* 60(12): 2575–80 (1982)). Immunological assays to detect various microorganisms including fungi using antibodies are also known, including those employing monoclonal antibodies reactive with antigens associated with particular organisms. (Goldstein, European Patent Application EP 176,355 (1986)). Such assays are not widely applicable because they are based on species-specific proteins including antigens. In addition, to detect the organism the assays typically require that the specific protein be isolated or exposed for reaction with the antibody in the assay.

There continues to exist a need for rapid and reliable detection of fungi and yeasts without requiring in vivo or in vitro culturing techniques or complex staining reagents, and that is applicable to a wide variety of organisms. The present invention satisfies these needs and provides related advantages as well.

SUMMARY OF THE INVENTION

The method of the invention is based on an application of the recognition that fungi and yeasts are rich in chitin, and the assay of the invention is for chitin detection. Unlike the prior art assays, the method is conducted in a fluid sample suspected of containing the organisms by attaching the sample to a solid phase, for example the bottom of a microtiter plate well or on the surface of a glass slide, contacting the bound sample with an agent capable of selectively binding to chitin in the sample, for example a lectin or antibody against chitin. The agent is or can be labeled to permit detection. The presence of the fungi is determined by detecting the label bound to the solid phase. The sample may be attached to the solid phase by drying and fixation using chemicals and or heat, thus obviating the need to isolate particular substances from the sample, prior to reaction with the labeled reagent in an assay. The method is not limited to particular species of fungi or yeasts since all such organisms contain chitin.

BRIEF DESCRIPTION OF THE DRAWINGS

The present invention will be described in connection with the accompanying drawings in which.

DETAILED DESCRIPTION OF THE INVENTION

Figure 1:
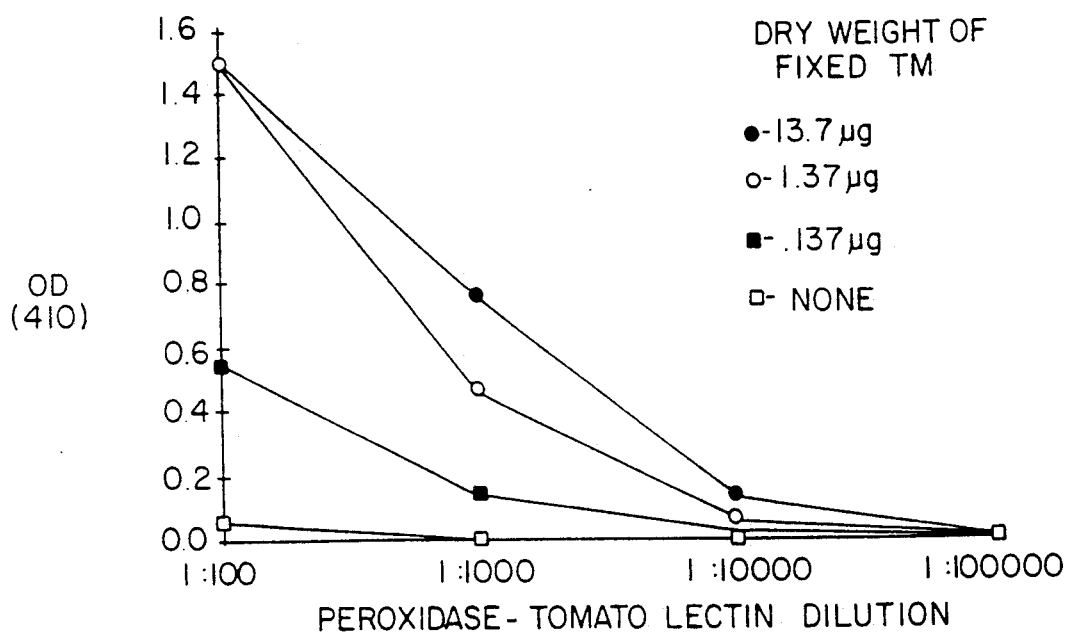
FIG. 1 is a graph demonstrating the binding of tomato lectin to *Trichophyton metangrophytes* using the assay of the invention.

The method of the present invention allows the rapid detection of the presence of a variety of fungi and yeast, without requiring costly and time-consuming culturing or staining of the organisms. The method provides an assay for detecting chitin using chitin-specific reagents and is not limited to any particular strain or species of organism. In addition, the method does not require that substances such as antigens be isolated from a sample suspected of containing organisms, prior to detection in the assay.

The substance that is detected in the method of this invention is chitin, a N-acetyl-glucosamine oligomer present in cell walls of nearly all fungi and yeasts.

In accordance with the method of the invention a sample suspected of containing target organisms, is obtained. The sample may originate from humans or animals and may be a biological fluid such as urine, spinal fluid or blood serum, or may be a biological specimen such as skin scrapings, sputum, tissue homogenates, wound exudates, or hair. In addition, samples may consist of materials from plants including tissue, scrapings, fluids, exudates and homogenates, or may be water or food suspected of contamination.

A sample suspected of containing fungi or yeast, is adsorbed onto a solid phase such as a glass slide, nitrocellulose filter, microtiter plate or other suitable surface by drying, and is adhered by fixation using heat or chemical fixatives, such as formalin, acetone or ethanol. Alternatively, the sample may be centrifuged to attach the non-fluid components onto the solid phase, for example, onto the bottom of microtiter wells; the fluid component may be removed by vacuum aspiration. Since chitin is generally insoluble, it will remain on the solid phase when the liquid is removed. A fixative, such as 10% neutral buffered formalin, may then be used to adhere the sample containing the organisms to the surface of the solid phase.

The sample can also be manually smeared onto a glass slide with a cotton swab, scalpel blade, or other similar device, allowed to dry completely and then fixed with chemicals. Heat may also be used for fixation, for example, the solid phase may be placed over a boiling (100° C.) water bath until the sample adheres onto the solid phase.

If the sample has no fluid component, it may be manually placed on the solid phase and adhered using chemical fixatives, or it may be suspended in a fluid and applied to a solid phase as described above. If the sample is a biopsy of an animal or plant tissue the material may be fixed in formaldehyde, embedded in paraffin wax and thin-sectioned. The sections may then be chemically fixed onto the solid phase as described above.

After attachment, binding sites on proteins contained in the sample are preferably blocked, for example by incubation of the fixed sample on the solid phase using an irrelevant protein solution such as bovine serum albumin (BSA), casein or egg albumin. Blocking reduces any non-specific electrostatic interactions of the binding sites which may interfere with the assay to detect chitin.

The assay of the invention relies upon binding of a reagent to chitin and the visualization of this binding by a labeling system. The binding reagents of the assay include lectin, such as tomato or potato lectin, and antibodies reactive with chitin ("anti-chitin" antibodies).

Lectins are proteins or glycoproteins that bind to particular sugars. Lectins that are useful in the assay set forth herein are those specific for chitin. Tomato lectin, for example, may be isolated from the common tomato (*Lycopersicon asculentum*) and has an approximate molecular weight of 71,000 daltons. It is composed of approximately equal amounts of protein and carbohydrate and binds with high affinity to oligomers of N-acetyl-glucosamine. It agglutinates human, mouse, and sheep erythrocytes and is not mitogenic for mouse lymphocytes.

Polyclonal antibodies reactive with chitin may be obtained by recovery of serum-containing antibodies following immunization of a mammalian host using chitin as the immunogen. Procedures for producing polyclonal antibodies are well known and will not be repeated here. The serum containing polyclonal antibodies is used for binding in the assay as described below to detect chitin-containing organisms.

Monoclonal antibodies reactive with chitin may also be used in the assay to detect chitin. These monoclonal antibodies may be derived using known techniques following the procedures of Kohler and Milstein, *Nature*, 256:495 (1975), incorporated by reference herein. In this procedure, hybridomas are prepared by fusing antibody-producing cells (typically spleen cells of mice previously immunized with an antigen) to cells from an immortal cell line such as myeloma cells, using somatic cell hybridization. The monoclonal antibodies are generated by immunizing a suitable host, for example a mouse, using chitin as the immunogen. The animal is then boosted two or more times with the immunogen. Spleens are harvested from the animals several days after the last boost, and a spleen cell suspension is prepared for fusion with murine myeloma cells using known fusion techniques. The hybridomas resulting from the fusion process are allowed to increase in number. Thereafter, the resulting supernatants are screened using immunoassay procedures to detect antibodies present in the supernatants that are capable of binding to chitin.

The assay to detect the presence of chitin-containing fungi, may be a direct binding assay in which the binding reagent, lectin or anti-chitin antibody, is reacted with chitin in fungi present in the sample, by contacting the sample attached to the solid phase with a labeled binding reagent. The label is then detected to determine whether fungi are present. In addition, the presence of fungi may be quantified, by using pre-determined amounts of the labeled assay reagent and relating the intensity of the signal produced by the label (which is a function of the amount of assay reagent reacted), to the concentration of chitin using standard binding curves. These curves are generated by measuring the intensity of the signal produced using known amounts of chitin.

The amount of chitin may also be quantified using an indirect, competitive inhibition assay in which a mixture of labeled assay reagent, for example lectin, and organism-containing solution is mixed and then added to react with chitin attached to the solid support. Chitin-containing organisms will compete with the immobilized chitin and thus reduce the degree of signal produced by the label in a dose related manner, permitting a determination of the amount of chitin present in the organisms in the sample.

Visualization of the binding of the assay reagent to chitin present in the sample, may be accomplished by directly labeling the lectin or the anti-chitin antibody assay with a substance capable of producing a signal, for example, a radionuclide, enzyme or a fluorescent agent, using known procedures. If an enzyme label is employed, an enzyme is selected which when reacted with its appropriate substrate produces a color or other visibly detectable signal. In those instances where the enzyme substrate is to be used in solution to contact the enzyme-labeled reagent bound to the sample on the solid phase, a soluble enzyme substrate such as ortho-phenylenediamine (OPD) reactive with the enzyme horseradish peroxidase (HRP) may be used. Alternatively, if the sample or specimen is applied manually to a solid phase such as a glass slide and is to be visualized, then a substrate such as diaminobenzedene or 3-amino-9-ethylcarbazole and the HRP is used. The colored, insoluble reaction product from the cleavage of the substrate by the enzyme will be deposited at or near the location of the enzyme. Thus when a fungal structure is coated with enzyme-labeled lectin or antibody, the enzymatic reaction will deposit the colored substrate around and on the fungal structure and allow the fungus to be readily detected by visual (microscopic) examination.

Alternatively, the assay reagent may be indirectly labeled, attaching the signal-producing label to an additional substance which binds to the assay reagent. For example, where lectin is used to detect the chitin, an anti-lectin antibody may be conjugated with label and bound to the lectin for reacting with the chitin. This assay may provide a more sensitive assay for the detection of the organism because more label can be bound per unit of assay reagent.

Biotin/avidin reagents may be used to signal binding. In this case, biotin is covalently bound to antibody, for example, anti-chitin antibody. The biotin-specific receptor protein avidin is conjugated to enzyme, then reacted with biotin to label the antibody. The labeled antibody is then used in an assay as described above.

The following examples are presented to illustrate the present invention and to assist one of ordinary skill in making and using the same. The examples are not intended in any way to otherwise limit the scope of the disclosure or the protection granted by Letters Patent hereon.

EXAMPLE I

Assay to Detect Fungus Using Lectin

Sample Preparation

The fungus *T. metangrophytes* was cultured in 100 ml Saboraud dextrose broth (DIFCO, Detroit, Mich.) at 26° C. for 18 days undergoing shaking at 100 cycles per minutes. Five ml of this culture was removed, diluted to 20 ml with PBS, and dispersed using a scintered glass homogenizer (Bellco Glass, Vineland, N.J.), washed three times by centrifugation and resuspended with PBS. The dry weight of the resulting suspension was determined by filtering 100 $\mu$l onto 0.2 $\mu$m filters (Millipore Corp., Bedford, Mass.), drying them overnight at room temperature, and determining the weight of the filter. The weight of the filter before filtration of the fungal suspension was substracted from the final weight of the filter to determine the weight of the sample. The concentration of the prepared sample was determined to be 13.7 mg/ml.

Concentrations of cell mass ranging from 13.7 mg/ml to 0.137 mg/ml were made by making serial ten-fold dilutions of the original dispersed fungal suspension. One hundred microliters of each dilution was dispensed into wells of microtiter plates (Immunon I, Dynatech Labs, Alexandria, Va.). After drying overnight at room temperature, the fungal cells were fixed to the bottom of the microtiter plate wells using neutral buffered formalin (pH 7.4), and washed three times with 0.01M PBS containing 0.05% Tween-20. The wells were then filled with 5% skim milk (as a source of bovine serum albumin and casein) to block non-specific binding sites on proteins present in the culture and to block unoccupied protein binding sites on the microtiter wells. The plates were incubated for 1 hour at 37° C., then washed three times with PBS containing 0.05% Tween-20.

Direct Labeling of Lectin 1500 units of horseradish peroxidase enzyme (Sigma Chemical Co., St. Louis, Mo.) were mixed with 500 $\mu$g of tomato lectin (Sigma Chemical Co., St. Louis, Mo.) in 500 $\mu$l of PBS. Glutaraldehyde (Sigma Chemical Co., St. Louis, Mo.) was added to a final concentration of 0.3% and incubated at 37° C. for two hours. The solution was then dialyzed against PBS and stored at 4° C. for up to 6 months.

Assay

To the blocked and washed microtiter plates, 50 $\mu$l of dilutions (1:$10^2$, 1:$10^3$, 1:$10^4$, 1:$10^5$) of the tomato lectin peroxidase conjugate were added and incubated for 1 hour at 37° C. The plates were washed three times with PBS +0.05% Tween-20 and to each well, 50 $\mu$l of a 1 mg/ml solution of OPD (Sigma Chemical Co., St. Louis, Mo.) in 0.1M citrate buffer (pH 5.0) containing 0.03% hydrogen peroxide, was added. Yellow color development was monitored visually for 20 minutes and recorded using an automated spectrometer (Microelisa Reader MR480, Dynatech Labs, Alexandria, Va.), at 410 nm.

Referring now to the Figures, FIG. 1 shows the ability of the peroxidase-conjugated tomato lectin to detect the presence of various concentrations of the fungus *T. metangrophytes* attached to the microtiter plates. The quantity of fungus (dry weight) and the concentration of lectin produced a dose-response relationship typical of standard binding phenomenon. The magnitude of the change in optical density of the substrate solution was directly proportional to the amount of fungus in each well and to the concentration of the lectin added to each well. This indicates that the color change was due to the binding of the lectin to chitin present in the fungus and was not due to random non-specific interactions.

EXAMPLE II

Specificity of Detection of Fungus Using Lectin

Figure 2:
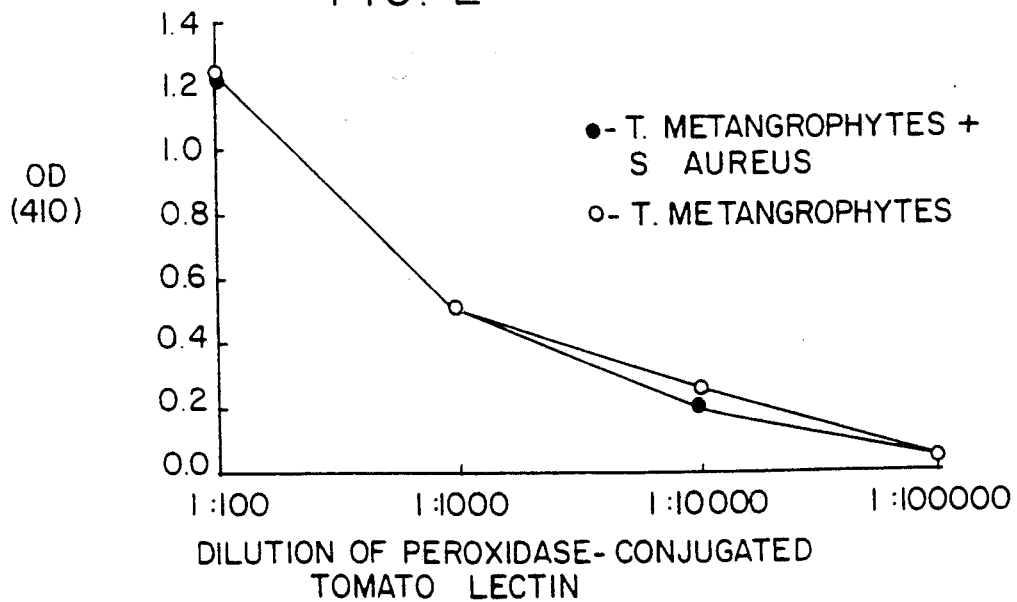
FIG. 2 is a graph of the binding specifity of tomato lectin for fungus in the presence of the bacteria *Staphylococcus aureus;*

To demonstrate the specificity of binding of lectin to fungi, the binding assay as conducted in Example I was performed with the additional presence of bacteria of *Staphylococcus aureus* (*S. aureus*). The bacteria were added to the concentrations of *T. metangrophytes* in solution prior to attachment of the fungus to the wells of microtiter plates. This addition resulted in approximately $10^6$ bacterial cells per well. The bacteria were attached to the wells along with the fungus using neutral buffered formalin, pH 7.4, after drying overnight. The wells were blocked with BSA using 5% milk, and washed with PBS containg 0.05% Tween 20. As shown in FIG. 2, no additional binding activity was produced by the presence of the bacteria, suggesting that all of the binding is due to fungal chitin and that little non-specific binding occurs.

EXAMPLE III

Assay to Detect Fungus Using Polyclonal Anti-Chitin Antibody

Sample Preparation

Samples of the fungus *T. metangrophytes* were prepared as described above in Example I.

Antibody Production

Balb/c mice were immunized with 100 $\mu$g chitin (Sigma Chemical Co., St. Louis, Mo.) emulsified in Incomplete Freund's Adjuvant (IFA) by both intraperitoneal (i.p.) and subcutaneous injection. Three weeks later the animals received a booster injection of 100 $\mu$g chitin in IFA i.p. Fourteen days later the animals were bled and the serum was collected and stored at $-20°$ C.

Assay

To microtiter plates blocked and washed as described above in Example I, various dilutions (1:$10^2$, 1:$10^3$, 1:$10^4$ and 1:$10^5$) of polyclonal antibody-containing sera were added and incubated at 37° C. for 1 hour. After washing, with PBS and 0.05% Tween 20, 50 $\mu$l of rabbit anti-mouse IgG antibody conjugated with HRP (Jackson Immunochemical, Avondale, Pa.) diluted 1:500 in PBS was added to each well and incubated for 1 hour at 37° C. The plates were then washed and to each well 50 $\mu$l of a 1 mg/ml solution of OPD in citrate buffer, pH. 5.0, containing 0.3% hydrogen peroxide was added. Yellow color development was monitored visually and recorded by an automated spectrometer.

Figure 3:
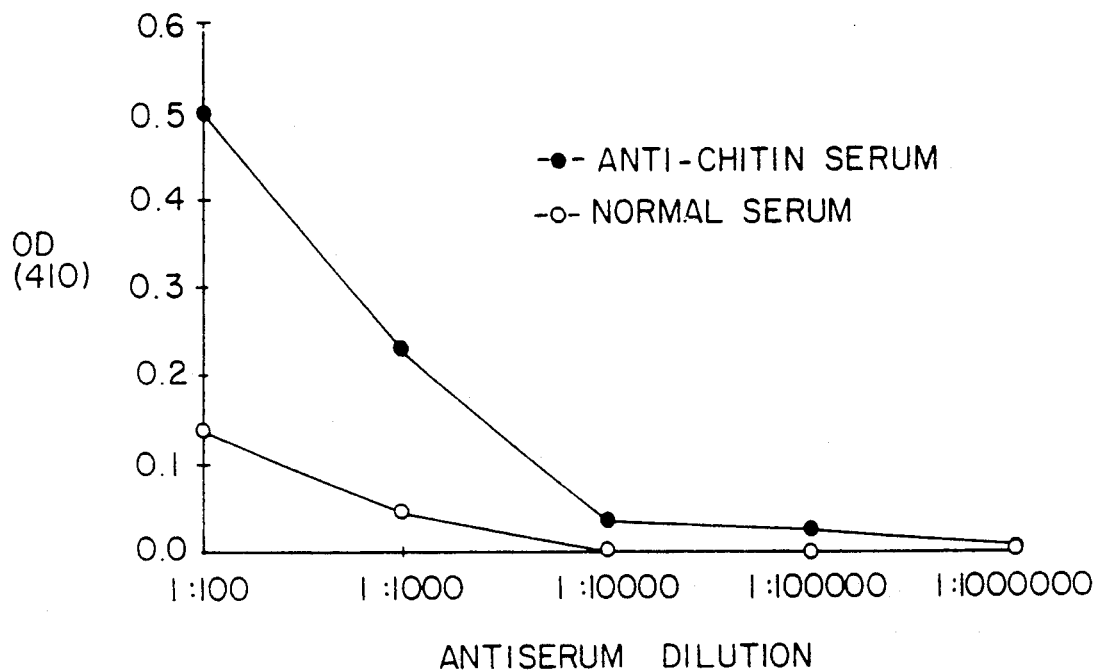
FIG. 3 is a graph showing the binding of mouse serum containing anti-chitin antibodies to *Trichophyton metangrophytes* using the assay of the invention.

FIG. 3 illustrates the ability of anti-chitin antibodies prepared as described above to detect the presence of *T. metangrophytes*. After only two immunizations the serum containing polyclonal antibodies from mice injected with chitin immunogen demonstrated a significant amount of binding activity against the fungus, as compared to normal serum from untreated mice.

EXAMPLE IV

Specificity of Detection of Fungus Using Anti-Chitin Antibodies

Figure 4:
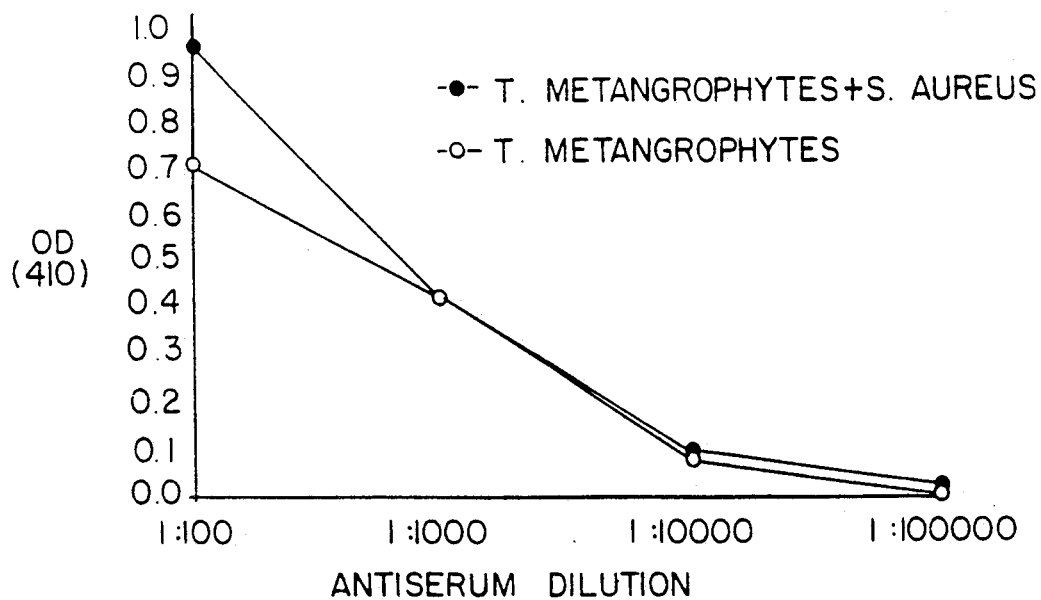
FIG. 4 is a graph of the binding specifity of antichitin antibodies for fungus in the presence of the bacteria *Staphylococcus aureus.*

To demonstrate the specificity of binding of antichitin antibodies to fungi, the binding assay as conducted in Example III was performed in the presence of bacteria. *S. aureus* were added to the fungal solution prior to attachment to the wells of the microtiter plates as described in Example III, resulting in approximately $10^6$ bacteria per well. After fixation and blocking as described above in Example I, washed plates were exposed to peroxidase-conjugated anti-chitin antibody prepared as described in Example III. FIG. 4 shows that while there is a slight increase in binding to bacteria-containing wells at higher dilutions of antibody ($1:10^2$), this binding disappears at lower dilutions and may be due to non-specific interactions or to endogenous peroxidase activity of the bacteria.

The above results indicate that the method of the present invention provides for specific detection of chitin-containing organisms such as fungi even in the presence of other organisms such as bacteria. The method is rapid and convenient without requiring isolation of a specific substance from the sample for use in an assay, or requiring lengthy culturing of fungal organisms for analysis, and may be performed in a laboratory or doctor's office with relative ease.

As will be apparent to those skilled in the art to which the invention is addressed, the present invention may be carried out by using techniques other than those specifically discussed above without departing from the spirit or essential characteristics of the invention. The particular materials and processes described above are therefore to be considered in all respects as illustrative and not restrictive. For example, labeling agents other than enzymes, such as radionuclides or fluorescing agents, may be used to detect the reagent bound to chitin using procedures known in the art. In addition, samples may be attached to a solid substrate by other procedures, for example filtration of a fluid sample and centrifugation of materials onto a solid phase. The scope of the present invention is as set forth in the appended claims rather than being limited to the examples of the methods and procedures set forth in the foregoing description.

What is claimed is:

1. A method for determining the presence of chitin-containing organisms in a sample which method comprises:
   (a) attaching a sample containing a fluid and nonfluid component and suspected of containing chitin-containing organisms onto a solid phase;
   (b) contacting said sample attached on the solid phase with a composition of anti-chitin antibodies which selectively binds chitin; and
   (c) detecting said antibodies bound to chitin present in the sample whereby the presence of chitin-containing organisms is determined.

2. The method of claim 1 wherein said step of attaching the sample onto a solid phase comprises adsorbing the non-fluid component of said sample onto the solid phase.

3. The method of claim 1 wherein said step of attaching the sample on a solid phase comprises the steps of:
   (a) drying said sample onto said solid phase; and
   (b) fixing said sample onto said solid phase to secure said sample on said solid phase.

4. The method of claim 3 wherein said step of fixing comprises using fixing reagents.

5. The method of claim 4 wherein said fixing reagents are selected from the group consisting of formalin, acetone, ethanol and acetic acid.

6. The method of claim 3 wherein said step of fixing comprises using heat.

7. The method of claim 1 wherein said solid phase is selected from the group consisting of filters, membranes, beads, particles, microtiter plates and slides.

8. The method of claim 7 wherein said solid phase is manufactured from the group of materials consisting of nylon, cellulose, nitrocellulose, plastics and glass.

9. The method of claim 1 wherein said sample is selected from the group consisting of skin, sputum, tissue homogenates exudates, and hair.

10. The method of claim 1 wherein said sample is a biological fluid from a human.

11. The method of claim 10 wherein said biological fluid is selected from the group consisting of urine, blood, and spinal fluid.

12. The method of claim 1 wherein said sample is water putatively contaminated with a chitin-containing organism.

13. The method of claim 1 wherein said sample is food putatively contaminated with a chitin-containing organism.

14. The method of claim 1 wherein said sample is obtained from a plant putatively contaminated with a chitin-containing organism.

15. The method of claim 1 wherein said composition of anti-chitin antibodies capable of binding chitin is antiserum raised against chitin.

16. The method of claim 1 wherein said composition of anti-chitin antibodies capable of binding chitin is a monoclonal antibody specific for chitin.

17. The method of claim 1 wherein said composition of anti-chitin antibodies is detected by means of a directly bound label selected from the group consisting of enzymes, fluorescent agents and radionuclides.

18. The method of claim 1 wherein said composition of anti-chitin antibodies is detected by means of an indirect label using substances capable of binding to said reagent, said substances labeled so as to be capable of detection.

19. The method of claim 18 wherein said composition of anti-chitin antibodies is bound to biotin and avidin reactive with said biotin is labeled so as to be capable of detection.

* * * * *